(12) United States Patent
Valsesia et al.

(10) Patent No.: US 10,408,727 B2
(45) Date of Patent: Sep. 10, 2019

(54) SCREENING OF NANOPARTICLE PROPERTIES

(71) Applicant: THE EUROPEAN UNION, represented by THE EUROPEAN COMMISSION, Brussels (BE)

(72) Inventors: Andrea Valsesia, Ranco (IT); Cloé Desmet, St Nicolas de Macherin (FR); Pascal Colpo, Angera (IT); François Rossi, Bergen (NL)

(73) Assignee: THE EUROPEAN UNION, REPRESENTED BY THE EUROPEAN COMMISSION, Brussels (BE)

( * ) Notice: Subject to any disclaimer, the term of this patent is extended or adjusted under 35 U.S.C. 154(b) by 11 days.

(21) Appl. No.: 15/571,808

(22) PCT Filed: Apr. 29, 2016

(86) PCT No.: PCT/EP2016/059633
§ 371 (c)(1),
(2) Date: Nov. 3, 2017

(87) PCT Pub. No.: WO2016/177641
PCT Pub. Date: Nov. 10, 2016

(65) Prior Publication Data
US 2018/0266932 A1    Sep. 20, 2018

(30) Foreign Application Priority Data

May 4, 2015 (EP) ..................................... 15166302

(51) Int. Cl.
*G01N 15/00* (2006.01)
*G01N 15/02* (2006.01)

(52) U.S. Cl.
CPC ......... *G01N 15/0227* (2013.01); *G01N 15/00* (2013.01); *B01J 2219/00619* (2013.01);
(Continued)

(58) Field of Classification Search
CPC .... B01J 2219/00274; B01J 2219/00722; B01J 2219/005; B01J 2219/00585;
(Continued)

(56) References Cited

U.S. PATENT DOCUMENTS

2004/0132214 A1    7/2004  Lin et al.
2005/0110990 A1*   5/2005  Koo ........................ G01J 3/44
                                                    356/301

(Continued)

FOREIGN PATENT DOCUMENTS

EP      1 785 718 A1    5/2007
WO  WO 2006/093055 A1    9/2006

OTHER PUBLICATIONS

Extended European Search Report for corresponding priority Application No. 15166302.8, dated Oct. 19, 2015 (7 sheets).
(Continued)

*Primary Examiner* — Michael P Stafira
(74) *Attorney, Agent, or Firm* — Lewis Roca Rothgerber Christie LLP (57) ABSTRACT

A nanoparticle screening chip and a method using said chip allowing for determining physical properties of nanoparticles, wherein the screening chip comprises a substrate having a working surface divided into a plurality of areas, wherein (1) each of these areas presents different surface properties defined by surface energy component (d,b,a), the total free energy $\gamma_{TOT}$ of the surface of each area being defined as follows: $\gamma_{TOT}=\gamma_{LW}+2(\gamma_+\gamma_-)^{0.5}$, wherein the components are: $\gamma_{LW}$=dispersive component=d, $\gamma_+$=electron acceptor component=b, $\gamma_-$=electron donor component=a;
(Continued)

and (2) each of these areas comprises a plurality of subareas, each subarea comprising an array of sub-micrometric holes or elongated grooves with a different aperture size (S1, S2, S3, ... ).

6 Claims, 3 Drawing Sheets

(52) U.S. Cl.
CPC .............. *B01J 2219/00621* (2013.01); *B01J 2219/00635* (2013.01); *B01J 2219/00637* (2013.01); *G01N 15/0205* (2013.01); *G01N 2015/0038* (2013.01)

(58) Field of Classification Search
CPC .... B01J 2219/00596; B01J 2219/00648; B01J 2219/00653; B01J 2219/00603; B01J 2219/00659; B01J 2219/00702; B01J 19/123; B01J 2219/0881; B01J 2219/1203; B01J 19/00; B01J 2219/00317; B01J 2219/00527; B01J 2219/00574; B01J 2219/00576; B01J 2219/00599; B01J 2219/00605; B01J 2219/00612; B01J 2219/00619; B01J 2219/00621; B01J 2219/00626; B01J 2219/0063; B01J 2219/00635; B01J 2219/00637; B01J 2219/00725; B01J 2219/00731; B01J 2219/00734; B01J 2219/00743; G01N 33/5438; G01N 33/5308; G01N 2458/10; G01N 33/5085; G01N 33/5088; G01N 2333/71; G01N 27/021; G01N 33/5008; G01N 33/533; G01N 33/566; G01N 33/57492; G01N 33/92; G01N 15/00; G01N 15/0205; G01N 15/0227; G01N 2015/0038; G01N 2030/8813; G01N 21/64; G01N 2333/43552; G01N 2500/04; G01N 27/4145; G01N 27/4146; G01N 27/447; G01N 33/5014; G01N 33/5058; G01N 33/54333; G01N 33/54346; G01N 33/58; G01N 33/6872

See application file for complete search history.

(56) References Cited

U.S. PATENT DOCUMENTS

| | | | |
|---|---|---|---|
| 2006/0160209 A1* | 7/2006 | Larson | B01L 3/502715 435/287.2 |
| 2009/0068757 A1* | 3/2009 | Lehmann | B01J 19/0046 436/172 |
| 2010/0177311 A1 | 7/2010 | Wada | |
| 2010/0201381 A1* | 8/2010 | Iqbal | A61B 5/14546 324/663 |
| 2010/0279289 A1* | 11/2010 | Chen | B82Y 5/00 435/20 |
| 2016/0069810 A1* | 3/2016 | Walavalkar | G01N 21/658 356/301 |
| 2016/0299134 A1* | 10/2016 | Denomme | G01N 33/54373 |

OTHER PUBLICATIONS

Replacement International Search Report and Written Opinion for corresponding International Application No. PCT/EP2016/059633, dated Oct. 31, 2016 (10 sheets).

* cited by examiner

SCREENING OF NANOPARTICLE PROPERTIES

CROSS REFERENCE TO RELATED APPLICATIONS

This application is a National Phase Patent Application of and claims priority to and the benefit of International Patent Application Number PCT/EP2016/059633, filed on Apr. 29, 2016, which claims priority to EP Patent Application Number 15166302.8, filed on May 4, 2015. The entire contents of both of which are incorporated herein by reference.

TECHNICAL FIELD

The present invention generally relates to nanoparticles and in particular to a method and device to rapidly determine certain properties of nanoparticles.

BACKGROUND ART

Extensive characterization of pristine nanomaterials (NMs), also called nanoparticles (NPs), is of importance to understand and control their interactions with biological systems. Indeed it becomes more and more apparent that NMs, besides their advantages in a large number of areas, potentially present negative effects on living organisms.

Indeed the NM surface hydrophobicity has e.g. been reported to have a critical role in the cellular uptake, toxicity, and immune responses to nanomaterials. NMs with a high degree of surface hydrophobicity were also shown to demonstrate severe hemolysis. According to some sources, NMs with decreasing surface hydrophobicities have an influence on plasma protein adsorption. Furthermore, in the development of nanoparticle-based vaccine adjuvants, the hydrophobicity of NMs was said to be a key factor for changing the interaction with immune cells.

Although these are only a few examples, it seems that main properties for which determination of reliable and reproducible data would be desirable are:

(1) NMs size and size distribution,
(2) Surface properties (surface charge, hydrophobicity), and
(3) Optical, mechanical, magnetic properties.

In particular, surface charge and hydrophobicity properties have shown to have direct effects on NMs functionality and toxicity.

Multiple characterization techniques allowing the characterization of NM properties exist, but there is currently no single method enabling the determination of the surface properties and the size distribution in one step.

NMs size and size distribution can be determined by using a combination of optical/imaging techniques, whereas surface properties can be determined with surface analysis techniques (XPS [X-ray photoelectron spectroscopy], ToF-SIMS [Time of Flight Secondary Ion Mass Spectrometry]). These methods are very sensitive, but unfortunately are time consuming and require expensive equipment and specialized expertise.

The constant increase of the NMs present in consumer products in a huge number of fields and the high number of new nanomedicines based on NMs make urgent the need to develop new tools enabling rapid characterization of NMs properties such as particular size, surface chemistry and hydrophobicity.

TECHNICAL PROBLEM

It is therefore an object of the present invention to provide an appropriate equipment and screening method for rapidly and easily identifying and/or quantifying a plurality of properties of nanoparticles, in particular size and preferably size distribution, surface charge and/or acidity and/or basicity, hydrophobicity and/or hydrophilicity.

GENERAL DESCRIPTION OF THE INVENTION

In order to overcome the above-mentioned problem, the present invention proposes in a first aspect a nanoparticle screening chip arranged for determining physical properties of nanoparticles, wherein the screening chip comprises a substrate having a working surface divided into a plurality of areas, wherein each of these areas presents different surface properties defined by surface energy component (d,b,a), the total free energy $\gamma_{TOT}$ of the surface of each area being defined as follows:

$$\gamma_{TOT} = \gamma_{LW} + \gamma_{AB} = \gamma_{LW} + 2(\gamma_+ \gamma_-)^{0.5}$$

wherein the components are:
$\gamma_{LW}$=dispersive component=d
$\gamma_{AB}$=acid base component, expressed by:
$\gamma_+$=electron acceptor component=b
$\gamma_-$=electron donor component=a
and each of these areas comprises a plurality of subareas, each subarea comprising an array of sub-micrometric holes or grooves with a different nominal aperture size (S1, S2, S3, . . . ).

In the nanoparticle screening chip of the invention, the number of areas preferably is from 5 to 100, more preferably from 10 to 50, whereas the number of subareas preferably is from 2 to 10, more preferably from 3 to 6.

Of course, the number of areas and subareas can be chosen to be higher than indicated above if so desired e.g. for increasing the finesse of the analysis, especially for complex samples with a huge number of different nanoparticles. However, the greater the number of areas and/or subareas, the greater the number of information to be captured and treated.

The substrate of the nanoparticle screening chip is preferably a highly flat substrate, preferably selected from glass or silicon. For dark field microscopy in reflection mode (see below), the substrate will further be chosen to be highly reflective, such as by depositing a one dimensional dielectric mirror or a flat gold or another noble metal on the substrate. As will be shown below, a so-called dark field setup for the determination is particularly advantageous; hence highly reflective substrates are particularly preferred.

In the nanoparticle screening chips of the invention, the surface properties (such as surface charge, hydrophobicity) of at least one area have been modified to capture nanoparticles having corresponding properties. Such a modification of the surface properties may be made by any appropriate means, such as plasma or ion beam treatments, wet chemistry, dip coating, spin-coating, self-assembly, etc. A particularly preferred means to modify the local surface properties is by plasma deposition of one or more layers of at least one optionally functionalized polymer with controlled surface properties. Non limiting examples are polytetrafluoroethylene (PTFE), polyethylene oxide (PEO), poly(acrylic acid) (PAA). The surface properties of the substrate can be then finely tuned and properly modified e.g. by using molecular self-assembly of polyelectrolytes, such as, poly (diallyldimethylammonium chloride) (PDDA) and poly(sodium 4styrene sulfonate) (PSS) and other polyelectrolytes normally used for surface properties modification. It is clear in the context of the present invention that the polymers or polyelectrolytes may be combined as desired or required to obtain surface properties suitable for discriminating the nanoparticles according to their physical properties.

As will be shown more in detail below, the inventors discovered that hydrophobic surfaces might not attract hydrophobic nanoparticles contained in an aqueous medium as they should, based on their hydrophobic nature. Surprisingly, by covering the hydrophobic layer by a thin superficial layer (<<100 nm) of hydrophilic compound, the overall affinity to hydrophobic NPs increases significantly. Hence, in a nanoparticle screening chip according to the invention, some of the areas are hydrophobic areas comprising one or more hydrophobic layer(s) may further comprise a superficial hydrophilic layer to increase their hydrophobic behavior.

In a second aspect, the invention discloses a method for screening nanoparticles to determine physical properties thereof, the method comprising the steps of
(a) feeding nanoparticles in solution/suspension over the working surface of a nanoparticle screening chip as described herein,
(b) incubating the nanoparticles in solution over the working surface during a time t and preferably thereafter rinsing the nanoparticle screening chip,
(c) determining physical properties of the nanoparticles by analyzing the nanoparticle screening chip by microscopy, preferably optical microscopy.

A first advantage of the invention is that the feeding of the nanoparticles in step (a) may be made in suspension or (colloidal) solution, which in the context of the present invention includes the original fluids the nanoparticles may be contained in, possibly after dilution if desired or necessary. So, for most applications, there is no need for complex or time-consuming preparation of the sample to analyze. Appropriate fluids can be any samples directly taken from the environment, airborne samples, such as surface or ground water or soil leaching; from the animal or human body, such as urine, blood, serum, sweat, tears, synovial fluid or saliva; from plants, such as oils, juices and other beverages; from food or from man-made products, such as paints, additives, lubricants, medicaments; etc. If required or desired, these samples may be diluted with an appropriate solvent. In a preferred application the device is used to regularly screen nanoparticles based products during their industrial manufacturing process as a quality control system to check NMs surface properties and average size, this is especially interesting for nanomedicine products.

The aim of the incubation in step (b) is to give the nanoparticles sufficient time to spread over the working surface and to reach those areas and subareas corresponding to their physical properties as further described herein. Hence this time t actually needed for good results may vary depending on a certain number of properties, among which the size/density of the NPs, their affinity with the solvent/suspension medium; the viscosity of the solvent/suspension medium, temperature, etc. In any case, the time t required for an appropriate incubation may be easily determined by the skilled person knowing that this time is the time to properly define the affinity of the NP with the different surfaces. In most cases, the time t will be between 2 seconds and 60 minutes, more generally however between 5 seconds and 45 minutes. In other cases, e.g. especially when the medium is viscous or the NPs have a fair affinity with the medium, the incubation time t may be chosen to be longer, such as up to 2 hours or even more.

In the method presented herein, the pH and/or the salt concentration of the nanoparticles containing solution or suspension is preferably adjusted in step (a) and/or in step (b).

As further explained below, the determination of the physical properties of the nanoparticles may further comprise the calculation of the surface properties of the nanoparticles by determining the acid-base and Lifshitz-Van der Waals surface free energy components ($\Delta G^{AB}_{adh}$ and $\Delta G^{LW}_{adh}$)

$$\Delta G_{adh}^{AB} = -2(\sqrt{\gamma_n^{AB}} - \sqrt{\gamma_l^{AB}})(\sqrt{\gamma_s^{AB}} - \sqrt{\gamma_l^{AB}})$$

$$\Delta G_{adh}^{LW} = -2(\sqrt{\gamma_n^{LW}} - \sqrt{\gamma_l^{LW}})(\sqrt{\gamma_s^{LW}} - \sqrt{\gamma_l^{LW}})$$

wherein AB (resp. LW) represents the acidbase (resp. Lifshitz-Van der Waals) interaction and $\gamma_{n(AB)}$, $\gamma_{l(AB)}$ and $\gamma_{s(AB)}$ (resp. $\gamma_{n(LW)}$, $\gamma_{l(LW)}$ and $\gamma_{s(LW)}$) are the acid base (resp. Lifshitz-Van der Waals) components of the surface energies of the nanoparticle (n), solution/suspension medium (l) and solid surface (s) of the area.

The determination of the physical properties of the nanoparticles can be done by any appropriate method, such as microscopy, by determining their location on the screening chip. The location within an area reflects the nanoparticle's surface properties (hydrophobicity and charge), whereas their location within particular subareas allows for deducing size and/or size distribution. Preferably, in step (c), the nanoparticle screening chip is inserted in a dedicated reading device allowing for optically determining the presence and the location of nanoparticles within the areas and subareas of working surface, wherein the reading device comprising a light source, a holding port arranged for holding said nanoparticle screening chip relative to said light source and a microscope enabling to measure the image of the working surface, preferably the reflection image of the working surface by means of a dark field microscope, more preferably further integrating a camera such as a CCD camera.

Still further aspects and embodiments of the invention relate to a nanoparticle screening chip reading device, configured for optically determining the presence and further physical properties of nanoparticles on a nanoparticle screening chip as described herein. Such a reading device generally comprises a light source, a holding port arranged for holding said nanoparticle screening chip in front of said light source, a (reflected) light detector and/or an imaging device. In a particular embodiment, the reading device comprises a microscope enabling to measure the reflection image of the whole working surface, preferably said microscope is operated in dark field configuration, advantageously in combination with a CCD camera.

The optical reading device is preferably characterized by a certain Field of View (FoV) and a Numerical Aperture (NA). The NA determines the angle of incidence of the detection light beam. For a given NA, flat areas (non-structured, without diffraction grating) will not reflect light and will appear black to the detector. On the contrary, areas with the diffraction grating will be reflected at a given wavelength, function of the geometrical parameter of the grating and the refractive index of the holes (with or without presence of NMs).

As a summary, it may be said that the present invention provides for (among others) a method and device allowing for the measurement of the NP properties through adsorption kinetics studies, that this is performed very elegantly and rapidly.

Indeed, to the contrary of the case of flat surfaces, the determination of the surface properties of NP is not well performed nowadays: it is done e.g. through measurement of adsorption of a dye (Bengal Rose) at different concentrations and measuring the adsorbed dye equilibrium concentration of adsorption. By measuring the slope (c−c0)/c0 for different c0 concentrations (c is the concentration of dye not adsorbed, c0 the total dye concentration) for a given number of nanoparticles, the slope gives a relative value of hydrophobicity. But it does not work for all hydrophobicity ranges and it does not give a hydrophobicity value in SI units.

Another method of measurement can be done by measuring the adsorption of NP on columns with a filler of different hydrophobicities. Here again, no absolute value of the surface energy components of the NP surface.

With the present invention, on the contrary, the surface energy component of the nanoparticle $\gamma^{LW}$ and $\gamma^{AB}$ are preferably calculated by multiparameter fitting of the total free enthalpy calculation based on the extended DLVO theory, knowing that the adsorption rate of NP on e.g. 16 different surfaces is proportional to the free enthalpy. So one measures the adsorption rates on these 16 different surfaces with known surface energy components, the free enthalpy of adsorption is calculated with 4 unknowns relative to the NP surface: $\gamma^{LW}$, $\gamma^+$ and $\gamma^-$ (which represent the two components of $\gamma^{AB}$) and the slope s of adsorption rate vs free enthalpy. It must be emphasized that the electrostatic interaction, if present, is known from the measurement of the Zeta potentials of the surface and the nanoparticles.

BRIEF DESCRIPTION OF THE DRAWINGS

Preferred embodiments of the invention will now be described, by way of example, with reference to the accompanying drawings in which:

FIG. 3 is a schematic representation of a further embodiment of a nanoparticle screening chip showing a plurality of areas (noted A01, . . . in FIG. 3(A)) with different dispersive, Acid-Base and charge properties, and within each of said areas are located subareas with different hole sizes (shown as three rectangles inside areas A01, A02 and A03, although not represented, each other of the areas preferably have the same or equivalent subareas);

Further details and advantages of the present invention will be apparent from the following detailed description of several not limiting embodiments with reference to the attached drawings.

DETAILED DESCRIPTION

Figure 1:
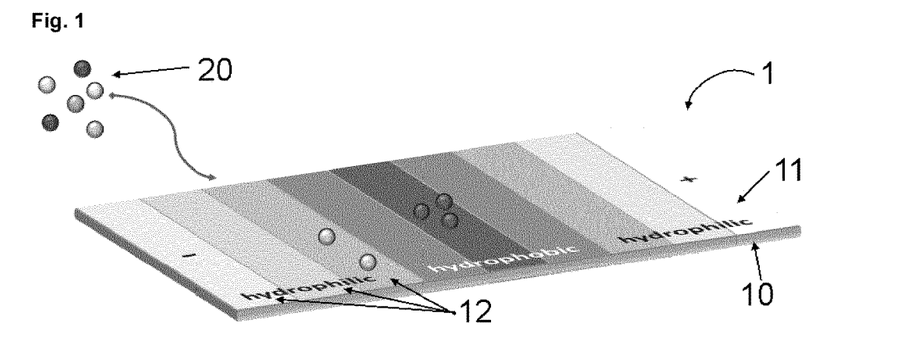
FIG. 1 is a schematic perspective view of an embodiment of a nanoparticle screening chip.
Figure 2:
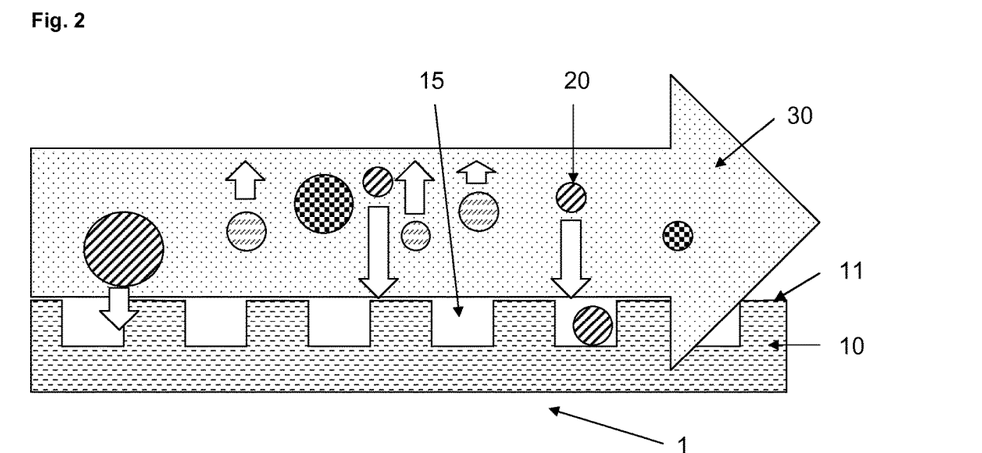
FIG. 2 is a schematic section across a further embodiment of a nanoparticle screening chip during feeding with a nanoparticle containing fluid.
Figure 3:
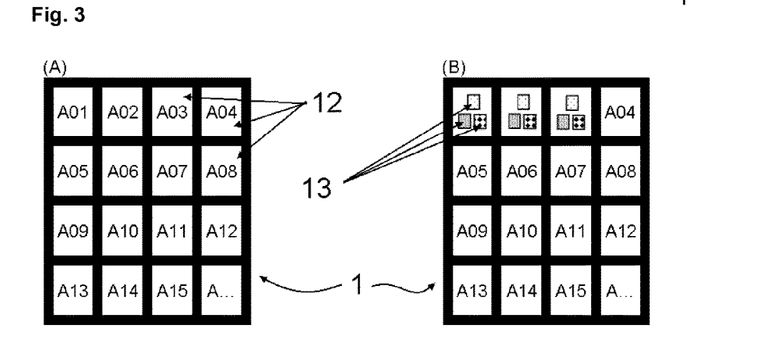

As depicted in FIG. 1-3, the method preferably uses a screening chip 1 (also called sensing chip) comprising an optically reflective substrate 10 with a (working) surface 11 provided with areas 12 having different surface properties.

As schematically represented in FIGS. 1 and 3, each area 12 is characterized by given values of the surface free energy components, the Total Free Energy of a solid surface being defined as:

$$\gamma_{TOT} = \gamma_{LW} + \gamma_{AB} = \gamma_{LW} + 2(\gamma_+ \gamma_-)^{0.5}$$

wherein the components are:
$\gamma_{LW}$ = dispersive (Lifshitz-van der Waals) component = d
$\gamma_+$ = electron acceptor component = b
$\gamma_-$ = electron donor component = a Each single area 12 of the surface can thus be defined by the three components (also called triplet) (d,b,a). The surface 11 of the sensing chip 1 can thus be characterized by a plurality of areas 12 and each of them presents different surface properties i.e. surface energy component (d,b,a).

Hence, NMs 20 in suspension or in a colloidal solution are characterized by the equivalent triplets of values of the surface energy according to their surface properties.

So, a triplet (d,b,a) can be defined for any given NM, (d,b,a)NMs.

As shown in FIG. 2, NMs 20 flowing (as indicated by horizontal arrow 30) along the sensing chip's surface 11 by means e.g. of a liquid cell will be attracted (illustrated by arrows pointing to surface 11) by the respective areas A=A(d,b,a) according to their surface properties (d,b,a) NMs. NMs having different surface properties will not be attracted or even be repulsed (arrows pointing away from surface 11) and thus stay within the liquid until they reach an area corresponding to their surface properties (d,b,a) NMs.

By this method, the (d,b,a) triplet of the NMs will be reconstructed according to the affinity of the NMs to the different areas with the corresponding surface properties.

Furthermore, each area 12 on the sensor chip is composed of different smaller areas (subareas 13) as shown in FIG. 3 (B) characterized by an array of sub-micrometric holes or grooves 15. Each subarea 13 is characterized by holes or grooves 15 with different aperture sizes, S, such as S1, S2, S3, . . . , Sn.

Each subarea 13 is characterized by a particular optical response, when illuminated by a beam of visible light at a certain angle of incidence and polarization. As a result of the nanograting, the incident light is diffracted at a given wavelength as a function of the refractive index of the hole or groove 15 containing or not the NMs. The presence of NMs 20 in the holes or grooves 15 can be thus monitored by measuring the wavelength of the diffracted light.

Hence, NMs 20 during their transport along the surface 11 of the chip 1 are attracted (or not) by hydrophobic or other forces towards the surface. Among the attracted NMs, only those with a diameter smaller than the aperture size of the holes S will be captured within the holes or grooves 15. NMs captured within the holes will locally change the refractive index of the nanoholes and modify the optical response of the grating. By monitoring the optical response, the presence of NMs with a diameter smaller than a certain size $S_{min}$ (hole size) are detectable.

The optical reader preferably consists of a microscope in dark field (DF) configuration, in particular with a CCD camera enabling to capture and to measure the reflection image of the whole sensing surface.

The optical reader is characterized by a certain Field of View (FoV) and a Numerical Aperture (NA). The NA determines the angle of incidence of the detection light beam. For a given NA, flat areas (non-structured, without diffraction grating) will not reflect light and will appear black to the detector. On the contrary, areas with the diffraction grating will be reflected at a given wavelength, function of the geometrical parameter of the grating and the refractive index of the holes (with or without presence of NMs).

When NMs fill the holes of the grating the reflected color of the area will change accordingly, so the presence of NMs in the holes can be by monitored by color changes visually or with a camera sensor.

In another aspect, the invention in particular relates to the sensing chip (nanoparticle screening chip) having the features as described herein.

According to the inventors, the main advantage of the invention is that the proposed solution enables the rapid screening of samples containing NMs. Indeed, the sensor will enable the detection within a few seconds (and with very limited sample amount, such as few hundreds of μl) the presence of NMs smaller than size $S_{min}$. Furthermore, the use of different $S_{min}$ within one subarea and hence the presence and proportion of NMs within one or more of the differently sized holes will provide information about NM size distribution. Together with the minimum size, the device will allow to characterize the surface property of the NMs, determining their acidic, basic or dispersive components, as well as their sizes and size distributions.

Below are described some experiments and considerations done in the context of making the present invention. These experiments provide further guidance for the skilled person in order to reduce to practice the present invention. The information below should however not be construed as limiting the invention to the particular embodiments and results described.

Experiments and Experimental Setup

A) Modification of the Surface Energy Components

A silicon substrate (it might be glass or any other flat surface) was modified by different plasma deposition in order to tune the surface hydrophobicity. Polytetrafluoroethylene was used to generate a hydrophobic surface, the deposition was realized using pure octofluorocyclobutane ($C_4F_8$) as the gas precursor at a pressure of 3.2 Pa (27 mTorr), applying a power of 142 W for 5 min. Plasma-polymerized acrylic acid was deposited as a hydrophilic surface, using acrylic acid as the gas precursor at a pressure of 2.1 Pa (16 mTorr), applying a bias power of 400 W for 5 min.

Polyelectrolyte Layer by Layer Deposition

In order to tune the surface hydrophobicity, a layer-by-layer deposition of two polyelectrolytes was realized. The plasma-modified substrates were incubated for 2 min in Poly(diallyldimethylammonium chloride) (PDDA) 2% solution in water or in Poly(sodium 4-styrene sulfonate) (PSS) 2% in water for the self-assembly deposition of each polyelectrolyte layer-by-layer, starting from PDDA (positively charged) and alternating with PSS (negatively charged). After each step, the substrate was rinsed with milliQ water and dried under nitrogen flow.

A first study was realized using 200 nm diameter polystyrene particles (Polybead® microspheres, Polysciences). Those commercial particles were chosen as a model because of the large range of sizes and surface functionalization (corresponding to different hydrophobicity and charges) offered by the provider. The non-modified particles are stabilized by sulfonate groups; they are negatively charged and hydrophobic.

The modified surfaces were incubated with the model particles in order to evaluate the binding, associated to the interaction forces between the particles and the surfaces. The experiment was realized using 16 different conditions of salt concentration ([NaCl]=0/1/10/100 mM) and pH (2/4/7/10) in aqueous solution in which the particles were dispersed at the original concentration. The incubation took place with the substrate fully immersed in the different solutions for 30 min, then rinsed thoroughly with milliQ water and dried under nitrogen flow. The surfaces were finally imaged with Scanning Electron Microscopy (SEM).

The same experiment was realized with polystyrene particles modified with hydroxyl groups. This surface modification conferred to the particles a higher hydrophilicity.

In order to study the selective binding of NPs on chemically modified surfaces, two set of samples have been prepared. A first set of Silicon samples had been coated first with a plasma deposited layer of PTFE and then several layers of polyelectrolyte (PPS/PDDA) for decreasing the hydrophobicity level. A second set of sample has been prepared with a starting layer of PAA. Theses samples have been modified as well with PE deposition to decrease the surface hydrophobicity.

The results of characterization are presented in Tables 1 and 2.

TABLE 1

Summary of the characterization of the PTFE modified surface

| | Contact angle (°) | Ellipsometry Height (nm) | AFM Roughness (nm) | Z-potential at pH 7 |
|---|---|---|---|---|
| PSS #3 | 19.8 ± 0.4 | 0.65 ± 0.01 | 0.76 ± 0.08 | −57.64 ± 0.31 |
| PDDA #3 | 37.4 ± 0.3 | 0.44 ± 0.01 | 0.85 ± 0.09 | −4.13 ± 0.33 |
| PSS #2 | 53.3 ± 0.8 | 0.69 ± 0.01 | 0.83 ± 0.08 | −62.37 ± 0.59 |
| PDDA #2 | 65.4 ± 0.6 | 1.11 ± 0.02 | 0.85 ± 0.09 | −4.93 ± 0.25 |
| PSS #1 | 64.6 ± 0.7 | 0.66 ± 0.01 | 0.48 ± 0.05 | −60.22 ± 0.90 |
| PDDA #1 | 79.3 ± 0.7 | 1.43 ± 0.02 | 0.45 ± 0.05 | −26.28 ± 0.24 |
| PTFE | 106.8 ± 0.4 | | 0.29 ± 0.03 | −61.18 ± 0.13 |

TABLE 2

Summary of the characterization of the PAA modified surface

| | Contact angle (°) | Ellipsometry Height (nm) | AFM Roughness (nm) | Z-potential at pH 7 |
|---|---|---|---|---|
| PSS #3 | 22.8 ± 0.4 | 0.65 ± 0.01 | 1.87 ± 0.19 | −62.60 ± 0.33 |
| PDDA #3 | 28.2 ± 0.6 | 0.44 ± 0.01 | 1.88 ± 0.19 | −6.53 ± 0.68 |
| PSS #2 | 25.2 ± 0.1 | 0.69 ± 0.01 | 1.09 ± 0.11 | −50.37 ± 0.92 |
| PDDA #2 | 30.9 ± 0.4 | 1.11 ± 0.02 | 0.77 ± 0.08 | 2.80 ± 0.15 |
| PSS #1 | 41.4 ± 0.8 | 0.66 ± 0.01 | 0.65 ± 0.07 | −47.36 ± 0.29 |
| PDDA #1 | 52.1 ± 0.5 | 1.43 ± 0.02 | 0.12 ± 0.01 | −5.04 ± 0.53 |
| PAA | 58.3 ± 0.5 | | 0.23 ± 0.02 | −78.12 ± 1.38 |

As shown in Table 1, the sample coated with PTFE plasma-deposited layer was highly hydrophobic, with a contact angle of 106°. For each polyelectrolyte layer the contact angle measurement showed a decrease in the hydrophobicity of the surface, from 80° (hydrophobic) for the first layer, to 20° (highly hydrophilic) for the $6^{th}$ layer. The ellipsometry (optical technique for investigating the dielectric properties of thin films) enabled to measure the thickness of each polyelectrolyte layer. The PSS layers were around 0.7 nm thick, and each PDDA between 1.4 and 0.4 nm, the first one being the thickest. The AFM provided information on roughness that was increasing with the first 3 layers from 0.3 to 0.8 before being stable around 0.8 nm for the last 3 layers. The z-potential was measured for different pH, for all layers a negative z-potential was obtained for the whole range of pH, especially for the PTFE non-modified and the PSS layers, and closer to neutral for the different PDDA layers. This result can be explained knowing that the PDDA is positively charged and the PDDA and PTFE negatively charged.

The experiments performed on the PAA modified surface (Table 2) showed the same trend. With a base layer of PAA more hydrophilic, one could indeed reach the same surface properties with an increase in hydrophilicity with the polyelectrolytes layers, a more important increase in roughness and a zeta-potential negative for all conditions. The 6$^{th}$ layer enabled to obtain close surface properties with two substrates of different properties, PTFE or PAA.

The XPS and ToF-SIMS analysis of the surface modifications by PTFE plasma deposition and layer-by-layer polyelectrolytes deposition was also performed (data not shown). The surface analysis through XPS experiments demonstrated the presence of the PTFE on the silicon substrate, and the ToF-SIMS experiment confirmed those observations, with an analysis that is more surface sensitive, the coverage of the silicon substrate with the PTFE plasma, and of the PTFE base layer with the 6 layers of polyelectrolytes.

Nanoparticles Binding Study
Hydrophobic Nanoparticles

Considering that the silicon substrates modified by plasma deposition of PTFE shows a high hydrophobicity, a first experiment was performed with hydrophobic particles in different conditions. The PS particles in 16 conditions of pH and ionic strength were incubated on the surface in order to evaluate the binding of hydrophobic particles with a hydrophobic surface, expected to be high because of the hydrophobic forces. The surfaces were then analyzed with SEM and the ratio of the surface coverage was calculated for the different conditions using ImageJ software. Those results are presented in Table 3.

TABLE 3

Surface coverage (%) of PS particles on PTFE, contact angle = 105°

|  |  | pH | | | |
|---|---|---|---|---|---|
|  |  | 2 | 4 | 7 | 10 |
| Z-potential |  | 3 | −32 | −54 | −140 |
| [NaCl] | 0 | 2.5 | 2.4 | 0.8 | 0.6 |
| mM | 1 | 2.1 | 0.2 | 0.1 | 0.9 |
|  | 10 | 5.6 | 6.6 | 0.1 | 0.0 |
|  | 100 | 2.5 | 27.0 | 2.8 | 0.3 |

Surprisingly, the binding rate was low for all conditions, with a slight trend to a higher binding for low pH and high salt concentration.

The low binding of NP on the hydrophobic PTFE surface was hypothetically attributed to the poor wettability of the PTFE surface with the creation of micro-bubbles, which impede the contact between the surface and the particles in the water suspension, preventing the hydrophobic forces to take place.

The negative charges at the surface of the PTFE layer and of the particles would indeed be decreased for low pH and high ionic strength, in those conditions the long range repulsion by electrostatic forces would then be drastically decreased, enabling the shorter range hydrophobic forces to take place.

The following hypothesis is proposed to understand the low binding for all conditions. The interface between the surface and the particles should be considered as multiple interfaces: since the particles are incubated in an aqueous solution, the water is playing an important role into the substrate-particles interaction with a substrate-water interface and another interface particles-water. The exposition of the highly hydrophobic substrate to water would generate micro-air bubbles to limit the contact, and the same would happen on the surface of the hydrophobic particles. Those micro-bubbles could create a physical barrier, preventing the particles to approach to the surface close enough for the hydrophobic interactions to take place. To limit the presence of those air bubbles enabling the water contact on the surface, the hydrophobicity should then be decreased.

In order to verify this hypothesis, the same experiments were performed with the PTFE surface modified with polyelectrolyte layers. Since the number of polyelectrolyte layers has a direct influence on the hydrophobicity (as seen with the contact angle measurements), it was possible to achieve four different degree of hydrophobicity, corresponding to contact angles of 105°, 70°, 50° and 20°. The observation of the surfaces after incubation of the particles showed a progressive increase of the binding, with a more and more important surface coverage of the surface for a decreasing contact angle. The calculated surface coverage by the particles for the lowest contact angle is presented in Table 4.

TABLE 4

Surface coverage of PS particles on PTFE + PE (6 layers), contact angle = 20°

|  |  | pH | | | |
|---|---|---|---|---|---|
|  |  | 2 | 4 | 7 | 10 |
| Z-potential |  | −3 | −49 | −60 | −100 |
| [NaCl] | 0 | 54.2 | 57.2 | 33.0 | 3.6 |
| mM | 1 | 40.4 | 37.8 | 30.5 | 30.9 |
|  | 10 | 49.2 | 43.4 | 48.0 | 47.6 |
|  | 100 | 83.3 | 64.3 | 55.1 | 51.5 |

Compared to the results without polyelectrolytes, the surface coverage by the particles is dramatically increased with the 6 polyelectrolytes layers. Moreover, the trend already observed is confirmed, with an important increase of the binding with the decrease in pH and the increase of ionic strength. To compare the binding rate obtained on a hydrophobic substrate+hydrophilic superficial layer with the binding rate on a hydrophilic substrate and to verify the theory of the long range interactions, another experiment was performed using the previously described plasma deposited PAA, with and without the polyelectrolyte modification. The degree of hydrophobicity was tuned from around 60° of contact angle without polyelectrolyte to 20° with six layers of polyelectrolytes. The different surfaces after incubation of hydrophobic polystyrene particles in the same conditions as before were observed by SEM and the results in terms of surface coverage is presented in Table 5 for PAA alone (a) and PAA with six layers of polyelectrolytes (b).

TABLE 5

Surface coverage of PS particles on a. PAA, b. PAA + PE

|  |  | pH | | | |
|---|---|---|---|---|---|
|  |  | 2 | 4 | 7 | 10 |
| | | a. PAA | | | |
| Z-potential |  | −26 | −45 | −78 | −83 |
| [NaCl] | 0 | 0.0 | 3.4 | 0.0 | 0.0 |
| mM | 1 | 0.9 | 0.1 | 0.0 | 0.0 |

TABLE 5-continued

Surface coverage of PS particles on a. PAA, b. PAA + PE

|  |  | pH | | | |
| --- | --- | --- | --- | --- | --- |
|  |  | 2 | 4 | 7 | 10 |
|  | 10 | 0.1 | 0.2 | 1.8 | 0.0 |
|  | 100 | 80.8 | 51.6 | 39.4 | 0.4 |
| b. PAA + PE | | | | | |
| Z-potential | | −20 | −50 | −63 | −53 |
| [NaCl] | 0 | 1.0 | 0.0 | 0.0 | 0.0 |
| mM | 1 | 43.1 | 0.0 | 0.0 | 0.0 |
|  | 10 | 32.0 | 0.6 | 0.0 | 0.1 |
|  | 100 | 59.3 | 54.2 | 19.9 | 27.5 |

As can be observed for both PAA alone and PAA+PE, the surface coverage is extremely low for most of the conditions, with salt concentration between 0 and 10, and all pH on PAA alone and pH 4 to 10 on PAA+PE. The trend already observed before is still present with an increase of the binding rate with the increase of ionic strength and the decrease of pH, but even more than before since the particles binding increases only in those extreme conditions. Comparing the results on the PAA and PTFE substrates without polyelectrolytes (Table 3 and 5a), it can be assumed that, with the highest ionic strength, the binding is more important on PAA than on PTFE because of the physical barrier existing because of the highly hydrophobic properties of the PTFE. But, the main difference appears to be between PTFE+PE and PAA+PE (Table 4 and 5b). Indeed, adding the polyelectrolytes layers induce a large increase in the binding on the hydrophobic substrate, whereas the change with polyelectrolyte on PAA is significant only for pH 2 with salt, showing that the hydrophilic superficial layer only permit the hydrophobic interactions to take place, resulting in the binding of the hydrophobic particles only on the hydrophobic substrate.

Figure 4:
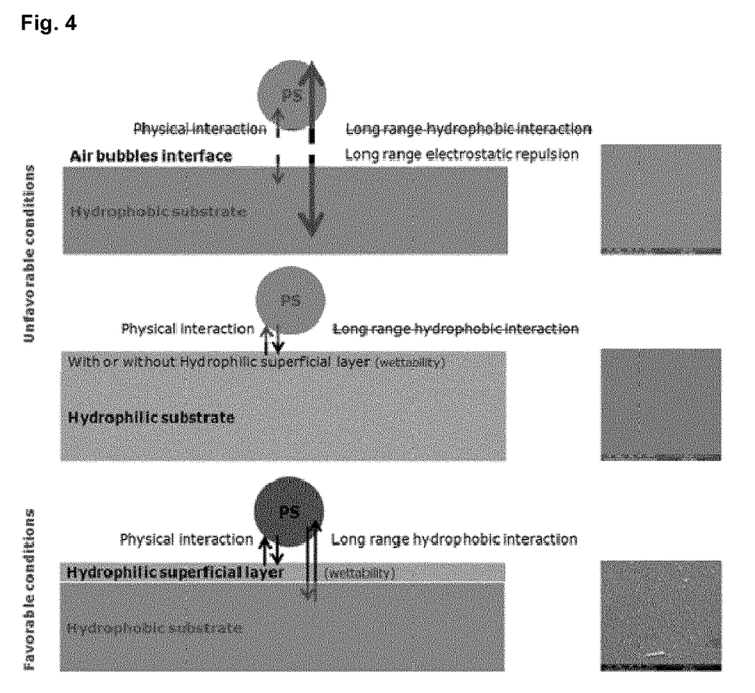
FIG. 4 is a schematic representation of unfavorable conditions preventing hydrophobic nanoparticles to bind to a hydrophobic surface, as well as a way to make these conditions more favorable.

A schematic interaction model of the long-range hydrophobic forces and the effect of the hydrophobicity of the substrate is presented in FIG. 4.

As presented in FIG. 4 showing the theoretical model of interactions according to different conditions, in the first tested case, the hydrophobic PTFE was in direct contact with the aqueous medium containing the particles. In this condition an air interface is generated to limit the contacts between water and the hydrophilic substrate, and this prevents the physical interaction between the particles and the substrate. In addition, if the electrostatic repulsion is not avoided through a decrease of pH and/or an increase of ionic strength, the hydrophobic interactions acting at shorter range can't take place. On the contrary, by minimizing the electrostatic repulsion thanks to low pH and high salt concentration, and enabling the physical interaction through the use of a superficial hydrophilic layer in top of the hydrophobic substrate, the most favorable conditions can be obtained for the binding of hydrophobic particles on the hydrophobic substrate. The hydrophilic layer has to be thin enough (<<100 nm) in order for the hydrophobic interactions to take place at the long range. The use of a polyelectrolyte layer is in this case a good way to obtain a high hydrophilicity with a thin coverage of the hydrophobic substrate. The superficial hydrophobicity/hydrophilicity degree, also called wettability, is therefore not driving the binding but enables the hydrophobic interactions to take place.

Hydrophilic Particles

The second part of the study consisted in the evaluation of the binding of hydrophilic particles on the previously used substrates. Considering that the system mechanism is based on hydrophobic interactions, its interest would be to enable to characterize the particles hydrophobicity thanks to different binding response on the patterned areas. The particles used for this part of the study were the same polystyrene particles but modified with hydroxyl groups which give them hydrophilic properties.

The PS—OH particles in 16 conditions of pH and ionic strength were incubated on the different surfaces. The analysis by SEM enabled then to calculate the ratio of the surface coverage for the different conditions. The results obtained on PTFE, PTFE+PE, PAA and PAA+PE are presented in Table 6.

TABLE 6

Surface coverage of PS-OH particles on a. PTFE, b. PTFE + PE, c. PAA, d. PAA + PE

|  |  | pH | | | |
| --- | --- | --- | --- | --- | --- |
|  |  | 2 | 4 | 7 | 10 |
| a. PTFE | | | | | |
| [NaCl] | 0 | 0.0 | 0.2 | 0.0 | 0.0 |
| mM | 1 | 0.0 | 0.0 | 0.0 | 0.0 |
|  | 10 | 6.9 | 0.0 | 0.0 | 0.0 |
|  | 100 | 0.0 | 0.6 | 4.0 | 0.0 |
| b. PTFE + PE | | | | | |
| [NaCl] | 0 | 0.3 | 0.2 | 0.0 | 0.0 |
| mM | 1 | 0.9 | 0.4 | 0.0 | 0.2 |
|  | 10 | 0.6 | 0.7 | 0.1 | 0.1 |
|  | 100 | 2.6 | 10.2 | 1.9 | 6.5 |
| c. PAA | | | | | |
| [NaCl] | 0 | 0.2 | 0.0 | 0.0 | 0.0 |
| mM | 1 | 0.8 | 0.5 | 0.0 | 0.0 |
|  | 10 | 0.2 | 0.1 | 0.1 | 0.0 |
|  | 100 | 36.5 | 51.7 | 22.2 | 1.6 |
| d. PAA + PE | | | | | |
| [NaCl] | 0 | 0.3 | 0.0 | 0.0 | 0.0 |
| mM | 1 | 0.3 | 0.0 | 0.0 | 0.0 |
|  | 10 | 2.3 | 0.1 | 0.0 | 0.0 |
|  | 100 | 54.0 | 37.8 | 1.0 | 1.4 |

As can be seen, the hydrophilic particles have a binding rate extremely low (<1% in most of the cases) for all conditions on the hydrophobic substrate, modified or not. On the hydrophilic substrate, modified with the polyelectrolytes or not, there is no binding in most of the conditions, with a significant binding only for high salt concentration and negative pH as already observed before. Those results confirm what was expected, with no hydrophobic interactions the hydrophilic particles did not bind to the different surfaces.

B) Method for the Determination of the Surface Free Energy of the (Unknown) Nanoparticles The generic method for the determination of the surface energy of an unknown sample of nanoparticles is similar to the extended DLVO model (Van Oss et al., J. Colloid Interface Sci. 111, 378-390).

When a nanoparticle in solution (many nanoparticles) gets in close contact with a surface there are different forces attracting or repelling the NP to/from the surface The forces are according $$F_{adh} = F^{LW} + F^{EL} + F^{AB}$$

With $F^{LW}$: Lifshitz-Van der Waals interaction force (attractive, short range)

$F^{EL}$: Electrostatic interaction force (attractive or repulsive, long range)

$F^{AB}$: Acid-base interaction force (hydrophobic interaction)

The Lifshitz-Van der Waals component is always attractive and always present.

The Electrostatic component can be attractive or repulsive, but anyway can be totally screened by the increase of the salt concentration. In any case, its values are known from the measurement of the Zeta potentials of the nanoparticles and the chip active surfaces. Between two surfaces with the same charge they are repulsive.

The AB forces include the hydrophobic interaction.

If one assumes that the attraction forces are ONLY the AB forces, they are long-range (acting when the NP is at several nm from the surface) and they are strong (this is controlled by the present experimental conditions).

The NPs are attracted to the surface and they stay there only if they are in a situation that minimizes the surface free energy of the system surface-liquid-NP. By definition:

l: liquid n: nanoparticle s: substrate

Interfacial Free Energies:

$\gamma_{sl}$ KNOWN $\gamma_{sn}$ MEASURED $\gamma_{nl}$ TO BE DETERMINED

Free energy of adhesion $\Delta G_{adh} = \gamma_{nl} - \gamma_{sn} - \gamma_{sl}$ The surface free energy balance ($\Delta G_{adh}$) is the balance between the interfacial energies (of the NP and the surface) with the liquid and the interface of the NP and the surface.

The present goal is to calculate the $\gamma_{nl}$ (the surface energy component of the NP, in particular the LW-hydrophobic component).

The geometric relationship between the surface components can be expressed as follows:

$$\Delta G_{adh}^{AB} = -2(\sqrt{\gamma_n^{AB}} - \sqrt{\gamma_l^{AB}})(\sqrt{\gamma_s^{AB}} - \sqrt{\gamma_l^{AB}})$$

$$\Delta G_{adh}^{LW} = -2(\sqrt{\gamma_n^{LW}} - \sqrt{\gamma_l^{LW}})(\sqrt{\gamma_s^{LW}} - \sqrt{\gamma_l^{LW}})$$

wherein AB (resp. LW) represents the acidbase (resp. Lifshitz-Van der Waals) interaction and $\gamma_{n(AB)}$, $\gamma_{l(AB)}$ and $\gamma_{s(AB)}$ (resp. $Y_{n(LW)}$, $Y_{l(LW)}$ and $Y_{s(LW)}$ are the acid base (resp. Lifshitz-Van der Waals) components of the surface energies of the nanoparticle (n), solution/suspension medium (l) and solid surface (s) of the area. $\gamma_{l(AB)}$ is known from the literature and $\gamma_{s(AB)}$ is known for each modified surface (and it is measured and known for each area of the device). $\gamma_{n(AB)}$ is the unknown parameter from the NP to be determined by the present method.

With the presented system, the $\Delta G_{adh}$ can be measured directly by measuring the kinetics of adsorption the nanoparticles on the surface. In particular $\Delta G_{adh}$ is proportional to the slope s of the kinetics of adsorption (see FIG. 5).

Hence, a preferred determination step of a method of the invention could be summarized as follows:

(a) One measures and one knows the surface properties of each surface
(b) One measures the kinetics of adsorption of the NP on each surface
(c) One calculates the surface properties of the NP.

C) Microfabrication of the Areas with Different and Controlled Surface Properties The areas characterized by controlled surface properties (as explained above) can be micro-patterned on a same surface e.g. by the following microfluidic device (MFD) designed by the inventors.

1) The surface of the chip can be modified by PTFE or PAA or any other polymer with controlled hydrophobicity/hydrophilicity,
2) The MFD is applied on top of the chip,
3) In each area of the MFD is flown as certain number of polyelectrolytes layers in order to locally modify the surface properties.

D) Nanofabrication of the Physical Filter or Capturing Features

The physical filters or capturing structures for the nanoparticles (holes arrays or grooves arrays) are nanofabricated on the surface of the chip e.g. by Ion Beam Milling, but the same structure can be made using different fabrication techniques.

The basic purpose is:

1) to create a diffraction grating (made of holes or grooves)
2) The same diffraction grating is filtering the NP
3) Only the NP smaller than the grating size can fall inside the grating
4) The optical response of the diffraction grating changes only when NP are located inside the grooves
5) In this way, particles smaller than a chosen size can easily be detected.

Figure 6:
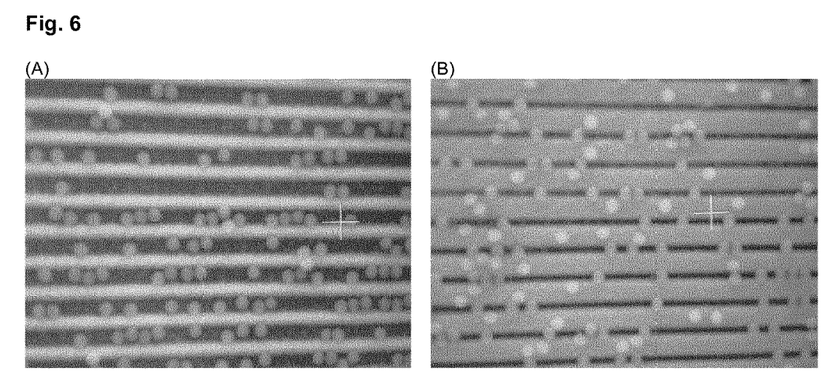
FIG. 6 are two SEM photographs of 200 nm nanoparticles, once on a substrate having grooves of 300 nm aperture (A) and once on a substrate having grooves of 100 nm aperture (B).

For example:

Grating 1 which has lines (grooves) of 300 nm wide is fed with 200 nm nanoparticles, Grating 2 which has lines of 100 nm wide is fed with 200 nm NP, It is clear that 200 nm NP will fall inside the 300 nm grooves, while they stay on top of the 100 nm grooves (See FIGS. 6 (A) and (B) which are SEM images of Polystyrene NP on a hydrophobic surface)

1) The optical response of the diffraction spectrum of the Grating 1 is modified by the presence of the NP in the grooves (FIG. 6(A))
2) The optical response of the diffraction spectrum of the Grating 2 is modified by the presence of the NP on top of the grooves (FIG. 6(B))

Figure 5:
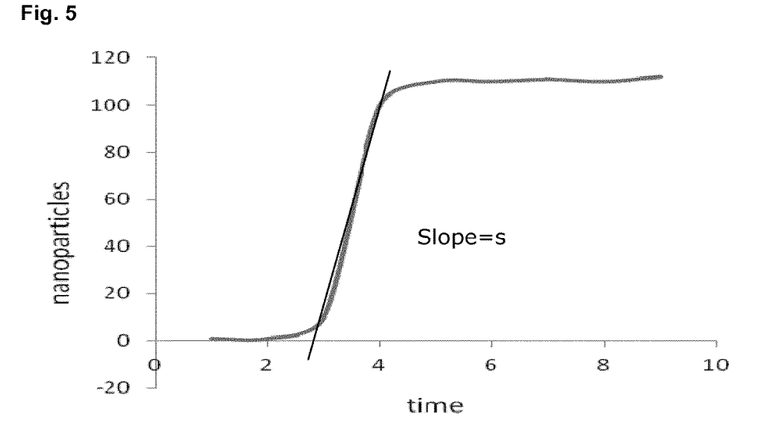
FIG. 5 is a diagram showing the kinetics of the binding of nanoparticles to a surface, the slope s (straight line) of the curve being proportional to the surface free energy balance $\Delta G_{adh}$.

The changes in the optical response can be following in real time during the NP adsorption and the kinetics curve can be reconstructed to calculate $\Delta G_{adh}$ (see above and FIG. 5). Moreover, it is possible to do a fast screening of the NP size.

E) Illustrative Optical Setup for the Real Time Detection of the NP on the Chip's Surface A preferred system to analyze the NP on the screening chip basically comprises of a dark field microscope with a large Field-of-view (to detect all the areas of the chip at the same time), which allows detecting NPs inside or outside the diffraction gratings and wherein the detection may be done in real time.

Figure 7:
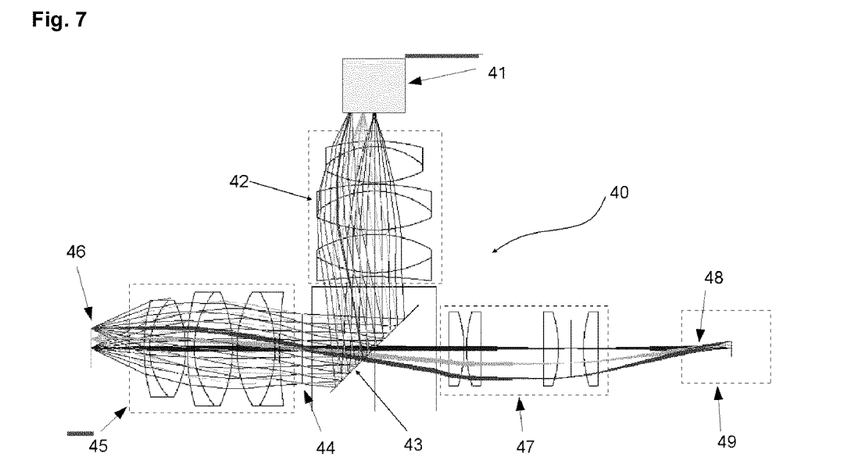
FIG. 7 is a schematic setup of a reading device useable for implementing a method as described herein in particular with a nanoparticle screening chip of the invention.

An example is shown in FIG. 7, wherein a light source 41 emits light passing through a first lens system 42, reflected by beam splitter 43 through illumination pupil 44 and a second lens system 45 onto the nanoparticle screening chip 46. The light which is refracted by the screening chip 46 passes through illumination pupil 44, splitter 43 and a third lens system 47 through the aperture 48 of a camera 49.

As an example, such a system may comprise:
from Edmund Optics/Thorlabs:
  two Erfle eyepieces 41-347 as lens systems 42 and 45
  50 mm beamsplitter cube 32-704 as beam splitter 43
  3-4 PCX (or achromatic pairs) lenses and lens mounting system (cage etc.) for lens system 47

Camera 49 may be a CMOS camera with standard lens (f~10 mm)

Imaging NA adjustable from the camera lens

As there is a common path for imaging and illumination between screening chip 46 and beam splitter 43, there may be some reflections to the image. In fact, the illumination angle can be adjusted by moving the hole plate in illumination pupil 44.

LEGEND

1 Nanoparticle screening chip
10 Substrate
11 Working surface
12 Areas
13 Subareas
15 Submicronic hole or groove
20 Nanoparticle(s)
30 Liquid flow
40 Dark field detection setup
41 Light source
42 First lens system
43 Beam splitter
44 Illumination pupil
45 Second lens system
46 Sample/screening chip
47 Third lens system
48 Imaging NA adjustment from camera lens
49 Camera

The invention claimed is:

1. A method for screening nanoparticles to determine physical properties thereof, the method comprising:
   (a) feeding a suspension or solution of nanoparticles to the working surface of the nanoparticle screening chip,
   (b) incubating the suspension or solution of nanoparticles on the working surface for an incubation time (t) and thereafter rinsing the nanoparticle screening chip, and
   (c) determining physical properties of the nanoparticles by analyzing the nanoparticle screening chip by optical microscopy.

2. The method according to claim 1, wherein the incubation time (t) is between 2 seconds and 60 minutes.

3. The method according to claim 1, wherein:
   the (a) feeding the suspension or solution of nanoparticles to the working surface further comprises adjusting the pH and/or salt concentration of the suspension or solution of nanoparticles; and/or
   the (b) incubating the suspension or solution of nanoparticles on the working surface further comprises adjusting the pH and/or salt concentration of the suspension or solution of nanoparticles.

4. The method according to claim 1, wherein the determining the physical properties of the nanoparticles further comprises calculating the surface properties of the nanoparticles by determining a surface free energy balance of an acid-base free energy component ($\Delta G^{AB}_{adh}$) and a Lifshitz-Van der Waals surface energy component ($\Delta G^{LW}_{adh}$), wherein $\Delta G^{AB}_{adh}$ is defined by Equation 2, and $\Delta G^{LW}_{adh}$ is defined by Equation 3:

$$\Delta G^{AB}_{adh} = -2\left(\sqrt{\gamma_n^{AB}} - \sqrt{\gamma_l^{AB}}\right)\left(\sqrt{\gamma_s^{AB}} - \sqrt{\gamma_l^{AB}}\right) \quad \text{Equation 2}$$

$$\Delta G^{LW}_{adh} = -2\left(\sqrt{\gamma_n^{LW}} - \sqrt{\gamma_l^{LW}}\right)\left(\sqrt{\gamma_s^{LW}} - \sqrt{\gamma_l^{LW}}\right) \quad \text{Equation 3}$$

wherein, in Equations 2 and 3:
   AB represents the acid-base interaction;
   $\gamma_{n(AB)}$, $\gamma_{l(AB)}$ and $\gamma_{s(AB)}$ are the acid base components of the surface energies of the nanoparticle (n), a medium of the suspension or solution (l) and the solid surface (s) of the area, respectively; and
   $\gamma_{n(LW)}$, $\gamma_{l(LW)}$ and $\gamma_{s(LW)}$ are the Lifshitz-Van der Waals components of the surface energies of the nanoparticle (n), the medium of the suspension or solution (l), and the solid surface (s) of the area, respectively.

5. The method according to claim 1, wherein the (c) determining the physical properties of the nanoparticles comprises inserting the nanoparticle screening chip in a reading device configured to optically determine the presence and location of nanoparticles within the areas and subareas of the working surface,
   wherein the reading device comprises a light source, a holding port configured to hold the nanoparticle screening chip in front of the light source, and a microscope configured to measure the reflection image of the working surface.

6. The method according to claim 1, wherein the incubation time (t) is between 5 seconds and 45 minutes.

* * * * *